United States Patent [19]

Angelchik

[11] Patent Number: 4,607,618

[45] Date of Patent: Aug. 26, 1986

[54] METHOD FOR TREATMENT OF MORBID OBESITY

[76] Inventor: Jean P. Angelchik, 1728 W. Glendale Ave., Phoenix, Ariz. 85021

[21] Appl. No.: 690,852

[22] Filed: Jan. 11, 1985

Related U.S. Application Data

[62] Division of Ser. No. 469,095, Feb. 23, 1983, abandoned.

[51] Int. Cl.$^4$ ............................................. A61B 17/00
[52] U.S. Cl. .................................... 128/1 R; 128/345
[58] Field of Search ............... 128/345, 341, 344, 1 R, 128/303 R

[56] References Cited

U.S. PATENT DOCUMENTS

| 115,252 | 5/1871 | Spencer | 273/58 D |
|---|---|---|---|
| 2,943,626 | 7/1960 | Dormia | 128/328 |
| 3,192,928 | 7/1965 | Horton | 128/341 |
| 4,416,267 | 11/1983 | Garren et al. | 128/344 X |
| 4,425,908 | 1/1984 | Simon | 128/345 X |

*Primary Examiner*—Michael H. Thaler
*Attorney, Agent, or Firm*—William H. Drummond

[57] ABSTRACT

Morbid obesity is treated by implacement in the fundus of a hollow shaped appliance. The appliance is formed of semi-rigid skeleton members and is collapsible to a dimension and shape which can be inserted into the stomach through the esophagus and cardiac opening. Upon release of the collapsed device in the stomach, it autogenously re-assumes its normal uncollapsed shape.

1 Claim, 7 Drawing Figures

METHOD FOR TREATMENT OF MORBID OBESITY

This application is a division of Ser. No. 469,095, filed Feb. 23, 1983 now abandoned.

This invention pertains to medical treatment methods and apparatus useful therein.

In a more particular respect, the invention concerns a method for treating morbid obesity.

In another particular respect, the invention concerns an appliance useful in such treatment.

In yet another respect, the invention relates to a bougie, adapted for inserting the appliance into the fundus of the stomach.

In the past, treatment of morbid obesity has been attempted by a variety of medical techniques, including, for example, removal of portions of the stomach and/or intestines, and stapling the stomach to reduce its volume. Such treatments either reduce the volume of food which can be comfortably ingested or the efficiency with which it is digested.

More recently, treatment methods have been proposed wherein the interior volume of the stomach is only temporarily reduced by causing the patient to swallow an inflatable balloon which is inflated after it reaches the stomach. According to this method, the inflated balloon serves to substantially reduce the interior volume of the stomach such that ingestion of a relatively small amount of food will cause distension of the stomach. Such distension causes excitation of certain neuroreceptors in the sub-mucosa of the stomach lying in the upper fundus. Excitation of these neuroreceptors, which are endings of the vagus nerves of the gastric plexus, causes the patient to experience the sensation of satiety even though the patient has ingested only a relatively small amount of food.

While such techniques have met with certain success they do suffer certain disadvantages, principally associated with the mechanical integrity of the balloon, inflation of the balloon and the need to remove the balloon periodically or after the treatment period.

It would be highly advantageous to provide medical methods for treatment of morbid obesity which simplify the insertion and removal of volume-reduction devices into and from the stomach and which more reliably provide the necessary volume reduction while minimizing untoward side effects caused by displacment of the devices within the stomach, accidental deflation, and the like.

It is, therefore, the principal object of the present invention to provide improved methods and apparatus for treatment of morbid obesity.

Yet another object of the present invention is to provide apparatus for conveniently inserting appliances useful in such treatment methods.

Still another object of the invention is to provide such methods and apparatus which function more reliably and with a minimum of opportunity for undesired side effects.

These and other, further and more specific objects and advantages of the invention will be apparent to those skilled in the art from the following detailed description thereof, taken in conjunction with the drawings, in which.

Briefly, in accordance with the present invention, I provide an intra-gastric appliance for the treatment of morbid obesity. The appliance comprises semi-rigid skeleton members joined to form a collapsible, hollow structure which is dimensioned and normally shaped to be received and retained within the fundus portion of the stomach. To facilitate implacement of the appliance, the structure is temporarily deformable by external force to a collapsed shape and cross-section, such that it is dimensionally compatible with per-oral implacement of the appliance through the esophagus and cardiac opening of the stomach. Upon release of the collapsing force, the appliance autogenously re-assumes its normal uncollapsed shape.

In accordance with another aspect of the invention, I provide a bougie for per-oral implacement of the appliance described above. The bougie comprises a hollow, generally cylindrical, flexible barrel portion having an open lower end. The barrel portion is cross-sectionally dimensioned to be inserted through the esophagus and the lower end thereof is dimensioned to receive and enclose the appliance and is adapted to exert and maintain inwardly directed circumferential force to maintain the appliance in the collapsed shape while it is received in the lower end of the bougie. A collapsed, rounded portion of the appliance protrudes from the lower open end of the bougie and acts as an obturator. Means are provided for ejecting the appliance from the lower end of the barrel portion into the fundus of the stomach.

In accordance with yet another aspect of the invention, I provide a method for treating morbid obesity which is an improvement upon the prior method involving implacement of a shaped device in the stomach to reduce the interior volume thereof. The improvement comprises implacing a shaped structure which is normally shaped and dimensioned to be received and retained within the fundus portion of the stomach and which has a deformable semi-rigid skeletal structure. The implacement of the collapsible structure is accomplished by collapsing the semi-rigid skeleton thereof by applying external force to deform the structure to a shape and cross-sectional dimension which is insertable through the esophagus and cardiac opening, per-orally inserting the collapsed structure into the fundus and relasing the collapsing force to cause the collapsed structure to autogenously re-assume its normal uncollapsed shape.

Figure 1:
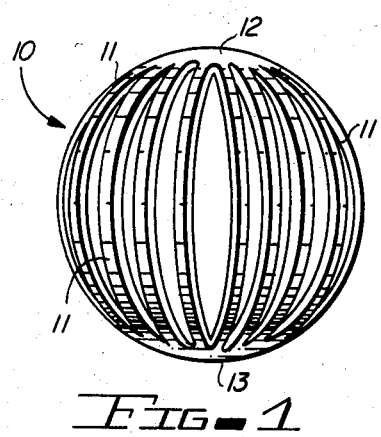
FIG. 1 is a perspective view of a collapsible applicance which is useful in accordance with the method of the invention, shown in its normal uncollapsed shape.
Figure 2:
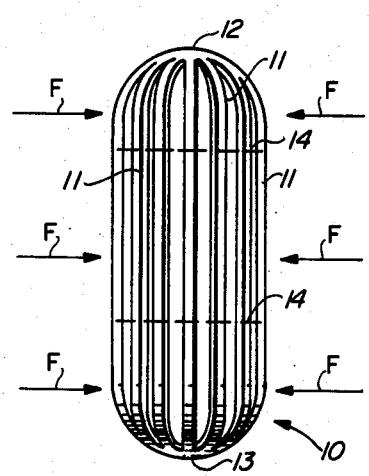
FIG. 2 is a perspective view of the appliance of FIG. 1 in the collapsed shape.

Turning now to the drawings, in which like reference characters identify the same elements in the several views, FIG. 1 illustrates the presently preferred embodiment of an appliance constructed in accordance with the invention. The appliance, generally indicated by reference numeral 10, simply consists of a plurality of normally semi-circular longitudinal skeleton members 11 joined at respective common ends 12 and 13 to form a collapsible hollow structure. As illustrated in FIG. 2, application of inwardly directed force F causes temporary deformation of the appliance from the spherical shape as shown in FIG. 1 to the elongate shape of reduced cross-section as shown in FIG. 2.

The force F (FIG. 2) can be applied and maintained in any convenient fashion, for example, by deforming the appliance by hand pressure and securing the appliance in the collapsed condition by tying dissolvable sutures around the circumference of the collapsed appliance at one or more points, as indicated by the dashed lines 14.

Figure 3:
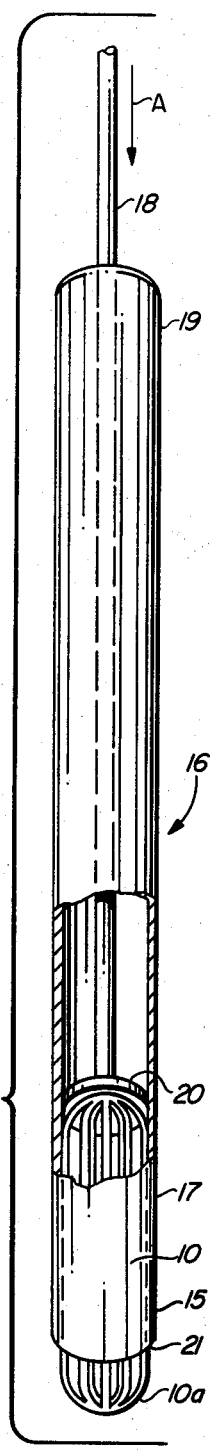
FIG. 3 is a partially cut-away view of a bougie-type device for inserting the appliance of FIGS. 1-2 into the stomach.

Alternatively, the device of FIG. 1 can be deformed by hand pressure and inserted into the lower end portion 15 of a bougie-type device (generally indicated by reference numeral 16), as shown in FIG. 3. The appliance 10, in the collapsed condition as shown in FIG. 2, is enclosed by the wall 17 of the bougie 16 which exerts inwardly directed circumferential force to maintain the appliance 10 in the collapsed condition shown in FIG. 2. The collapsed, rounded lower end 10a of the appliance 10 protrudes from the bougie 16, acting as an obturator. The bougie device 16 also includes a suitable ejector rod 18, operable through the upper end 19 of the bougie. Movement of the rod 18 in the direction of the arrow A exerts force on an internal piston portion 20 formed on the lower end of the rod 18 which, in turn, exerts force upon the collapsed appliance 10, causing it to be ejected from the bougie 16 through the open lower end 21 thereof.

Figure 4A:
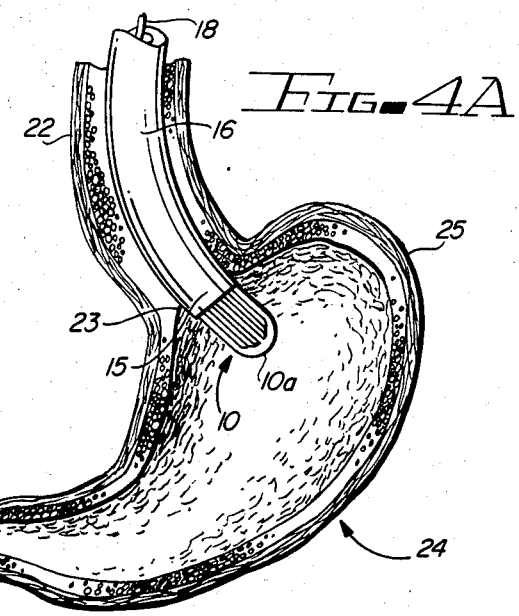
FIGS. 4A and 4B are sectional views of the stomach and esophagus illustrating insertion and final placement of the device of FIGS. 1-2 into the fundus of the stomach utilizing the bougie of FIG. 3.

As shown in FIG. 4A, the bougie 16 is per-orally inserted through the esophagus 22 and the cardiac opening 23 of the stomach (generally indicated by reference character 24). Movement of the ejector rod 18 causes the collapsed appliance 10 to be displaced from the lower end 15 of the bougie 16 in the fundus 25 of the stomach 24.

Figure 4B:
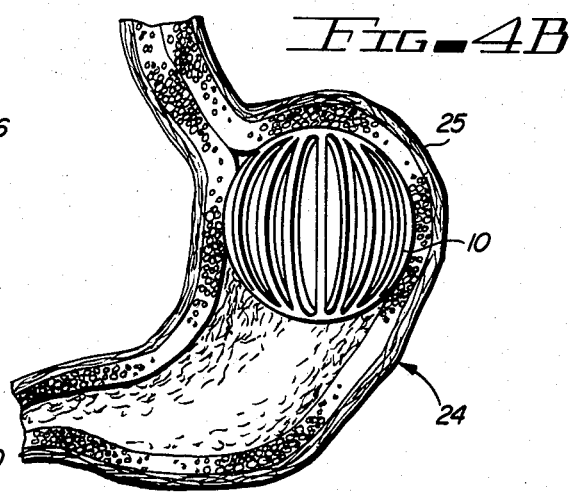

As shown in FIG. 4B, the appliance 10, after it is completely ejected from the lower end of the bougie, autogenously re-assumes its normal shape as shown in FIG. 1 and is received and retained within and substantially occupies the interior volume of the fundus 25, thereby reducing the total interior volume of the stomach by upwards of 30%-50%.

Figure 5:
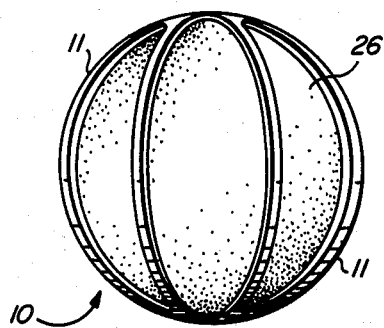
FIGS. 5 and 6 are partially cut-away perspective views of appliances constructed in accordance with alternate embodiments of the invention.
Figure 6:
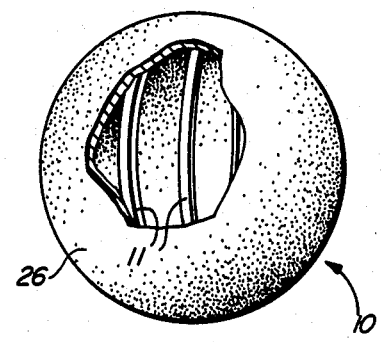

Alternative embodiments of the appliance of FIG. 1 are illustrated in FIGS. 5 and 6.

In certain instances, as where the appliance is intended to remain in the stomach for extended periods of time, it may be desirable to enclose the hollow structure by means of a flexible integument 26, either attached to the inside surfaces of the skeleton members 11 (as shown in FIG. 5) or to their outer surfaces (as shown in FIG. 6). During insertion, the integument 26 is pleated and folded into the interior of the appliance 10 so as not to interfere with the insertion of the appliance in the bougie or its ejection therefrom into the fundus. The integument will prevent the formation of a bezoar in the interior of the appliance 10.

In order to enhance and maintain the accuracy of placement of the appliance in the stomach, the appliance can be constructed of lightweight or hollow materials which will float in the liquids within the stomach. The materials of construction of the appliance are not highly critical so long as they are compatible with the body tissues and fluids involved.

Removal of the appliance can be effected by various means including surgical invasion or retrieval through the esophagus by endoscopic techniques. In certain applications, it may be desirable to form the entire appliance of biodegradable materials such that the device will dissolve after a pre-selected period of time in the stomach and be passed from the body through the digestive tract.

Having described my invention in such terms as to enable those skilled in the art to understand and practive it, and having identified the presently preferred embodiments thereof,

I claim:

1. In a method for treating morbid obesity, including the step of implacing a shaped device in the stomach, the improvement comprising:
   (a) providing a collapsible, hollow, shaped device, said device
      (i) being normally shaped and dimensioned to be received and retained within the fundus without deforming the stomach walls beyond its normal shape and dimensions,
      (ii) being formed of a semi-rigid skeleton which is collapsible by the application of external force to deform said device to a shape and cross-sectional dimension which is insertable into the stomach through the esophagus and the cardiac opening,
      (iii) being capable of autogenously reassuming and retaining said normal shape when such collapsing external force is removed;
   (b) collapsing said semi-rigid skeleton device by applying such external force to said shape and cross-sectional dimensions for insertion through the esophagus and cardiac opening;
   (c) per-orally inserting said collapsed structure into the fundus of the stomach through the esophagus and cardiac opening;
   (d) releasing said collapsing force to cause said collapsed skeleton structure to autogenously reassume and retain its normal shape; and
   (e) maintaining said device within the stomach for a length of time sufficient to cause a substantial weight loss by the patient.

* * * * *